US011297411B2

(12) United States Patent
Columbus

(10) Patent No.: US 11,297,411 B2
(45) Date of Patent: Apr. 5, 2022

(54) MICROPHONE UNITS WITH MULTIPLE OPENINGS

(71) Applicant: HEWLETT-PACKARD DEVELOPMENT COMPANY, L.P., Spring, TX (US)

(72) Inventor: Owen P. Columbus, Spring, TX (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 16/965,102

(22) PCT Filed: Mar. 30, 2018

(86) PCT No.: PCT/US2018/025474
§ 371 (c)(1),
(2) Date: Jul. 27, 2020

(87) PCT Pub. No.: WO2019/190559
PCT Pub. Date: Oct. 3, 2019

(65) Prior Publication Data

US 2021/0037310 A1 Feb. 4, 2021

(51) Int. Cl.

| | |
|---|---|
| ***A61F 11/06*** | (2006.01) |
| ***G10K 11/16*** | (2006.01) |
| ***H03B 29/00*** | (2006.01) |
| ***H04R 1/10*** | (2006.01) |
| ***H04R 1/04*** | (2006.01) |

(52) U.S. Cl.
CPC ............ *H04R 1/1083* (2013.01); *H04R 1/04* (2013.01); *H04R 2201/003* (2013.01); *H04R 2460/01* (2013.01)

(58) Field of Classification Search
CPC ................................ H04R 1/1083; H04R 1/04
See application file for complete search history.

(56) References Cited

U.S. PATENT DOCUMENTS

| | | | | |
|---|---|---|---|---|
| 6,732,588 | B1 | 5/2004 | Mullenborn | |
| 7,298,859 | B1 | 11/2007 | Worley | |
| 8,520,878 | B2 | 8/2013 | Inoda | |
| 2009/0218668 | A1 * | 9/2009 | Zhe | H01L 24/48 257/680 |
| 2010/0052082 | A1 * | 3/2010 | Lee | B81B 7/0061 257/416 |

(Continued)

FOREIGN PATENT DOCUMENTS

| | | |
|---|---|---|
| CN | 103200508 | 6/2013 |
| CN | 106937195 | 7/2017 |

(Continued)

*Primary Examiner* — Simon King
(74) *Attorney, Agent, or Firm* — Mannava & Kang PC

(57) ABSTRACT

According to examples, an apparatus may include a chamber having a hole and a microphone unit. The microphone unit may include a first substrate having a first opening aligned with the hole of the chamber, a second substrate positioned with respect to the first substrate to form a gap between the second substrate and the first substrate, the second substrate having a second opening, and a diaphragm housed within the gap formed between the first substrate and the second substrate, in which the first opening is positioned on a first side of the diaphragm and the second opening is positioned on a second side of the diaphragm.

15 Claims, 4 Drawing Sheets

(56) References Cited

U.S. PATENT DOCUMENTS

| | | | | |
|---|---|---|---|---|
| 2010/0183174 | A1 | 7/2010 | Suvanto | |
| 2011/0170699 | A1* | 7/2011 | Schoerkmaier | G10K 11/17875 381/71.1 |
| 2011/0172001 | A1* | 7/2011 | Schoerkmaier | H04M 1/035 455/575.1 |
| 2011/0176698 | A1* | 7/2011 | Tanaka | H04R 1/38 381/355 |
| 2012/0308066 | A1 | 12/2012 | Chen | |
| 2013/0070951 | A1 | 3/2013 | Tanaka et al. | |
| 2013/0140655 | A1* | 6/2013 | Yeh | H01L 21/56 257/416 |
| 2013/0161702 | A1* | 6/2013 | Chen | B81C 1/00246 257/254 |
| 2015/0125003 | A1* | 5/2015 | Wiesbauer | H04R 19/005 381/111 |
| 2015/0256940 | A1 | 9/2015 | Dehe | |
| 2015/0358708 | A1* | 12/2015 | Axelsson | H04R 1/1083 381/71.7 |
| 2016/0037263 | A1 | 2/2016 | Pal et al. | |
| 2017/0369305 | A1* | 12/2017 | Suvanto | B81B 7/008 |
| 2018/0041828 | A1* | 2/2018 | Sibbald | G10K 11/17857 |
| 2018/0048951 | A1* | 2/2018 | Zheng | H04R 19/04 |
| 2018/0115811 | A1* | 4/2018 | Zhang | H04R 1/086 |
| 2019/0047849 | A1* | 2/2019 | Park | B81B 3/0013 |
| 2019/0230446 | A1* | 7/2019 | Schultz | H04R 3/04 |
| 2020/0084550 | A1* | 3/2020 | Chiang | H04R 19/005 |
| 2020/0112800 | A1* | 4/2020 | Lee | H04R 19/005 |
| 2020/0196065 | A1* | 6/2020 | Pedersen | H04R 19/04 |
| 2020/0245077 | A1* | 7/2020 | Loeppert | H04R 19/005 |
| 2020/0252716 | A1* | 8/2020 | Pedersen | B81B 3/0027 |
| 2020/0255284 | A1* | 8/2020 | Kueffner | H04R 31/00 |
| 2020/0322732 | A1* | 10/2020 | Lee | H04R 31/00 |
| 2021/0219060 | A1* | 7/2021 | Qi | H04R 1/00 |

FOREIGN PATENT DOCUMENTS

| | | | |
|---|---|---|---|
| EP | 2249583 | A3 | 12/2014 |
| GB | 2526945 | B | 4/2017 |
| WO | WO-2011012360 | | 2/2011 |
| WO | WO-2017147545 | | 8/2017 |

* cited by examiner

MICROPHONE UNITS WITH MULTIPLE OPENINGS

BACKGROUND

Microphone units generally convert input audio signals into electrical signals and output the electrical signals to various types of audio input devices. The audio input devices may include, for instance, a mobile telephone, a transceiver, information processing systems, a recording device, etc. Some microphone units employ noise-canceling technology to suppress background noise and improve the accuracy of the electrical signals converted from the input audio signals.

BRIEF DESCRIPTION OF THE DRAWINGS

Features of the present disclosure are illustrated by way of example and not limited in the following figure(s), in which like numerals indicate like elements, in which.

DETAILED DESCRIPTION

For simplicity and illustrative purposes, the present disclosure is described by referring mainly to examples. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on.

Top or bottom ported microelectromechanical systems (MEMS) microphones may utilize a sealed can that includes a single opening (port) that exposes a MEMS diaphragm to external sound pressure variations. The rear volume contained inside the sealed can, which is behind the diaphragm, may define the natural low frequency roll-off and subsequently the low frequency phase response of the MEMS microphone. The size of the rear volume may also impact the noise floor of the MEMS microphone. Smaller rear volumes may result in higher rolloff frequencies, more phase shift and higher noise levels, while larger rear volumes may result in lower rolloff frequencies, less phase shift and lower noise levels.

Some microphone manufacturers may produce microphones with significantly larger cans to improve the low frequency performance and noise of their microphones, which may improve the accuracy of feedback microphones used in active noise canceling headphones. However, the larger cans may result in the microphones becoming physically larger and may thus be harder to integrate into constrained acoustic designs. This may especially be applicable to a feedback microphone in active noise canceling headphones, e.g., in-ear types of active noise canceling headphones.

Disclosed herein are apparatuses having chambers that may be implemented to improve the low frequency performance and noise of microphone units included in the apparatuses. That is, the chambers may have a larger size than the microphone units and the microphone units may include openings that are aligned with holes in the chambers such that reverberations of the diaphragms in the microphone units may be delivered into the chambers. The chambers may thus effectively provide a larger rear volume to the microphone units without causing the microphone units to be fabricated with larger cans. In other words, the microphone units disclosed herein may have improved low frequency performance as compared with microphone units of similar size and may thus be implemented in apparatuses having smaller sizes.

Figure 1:
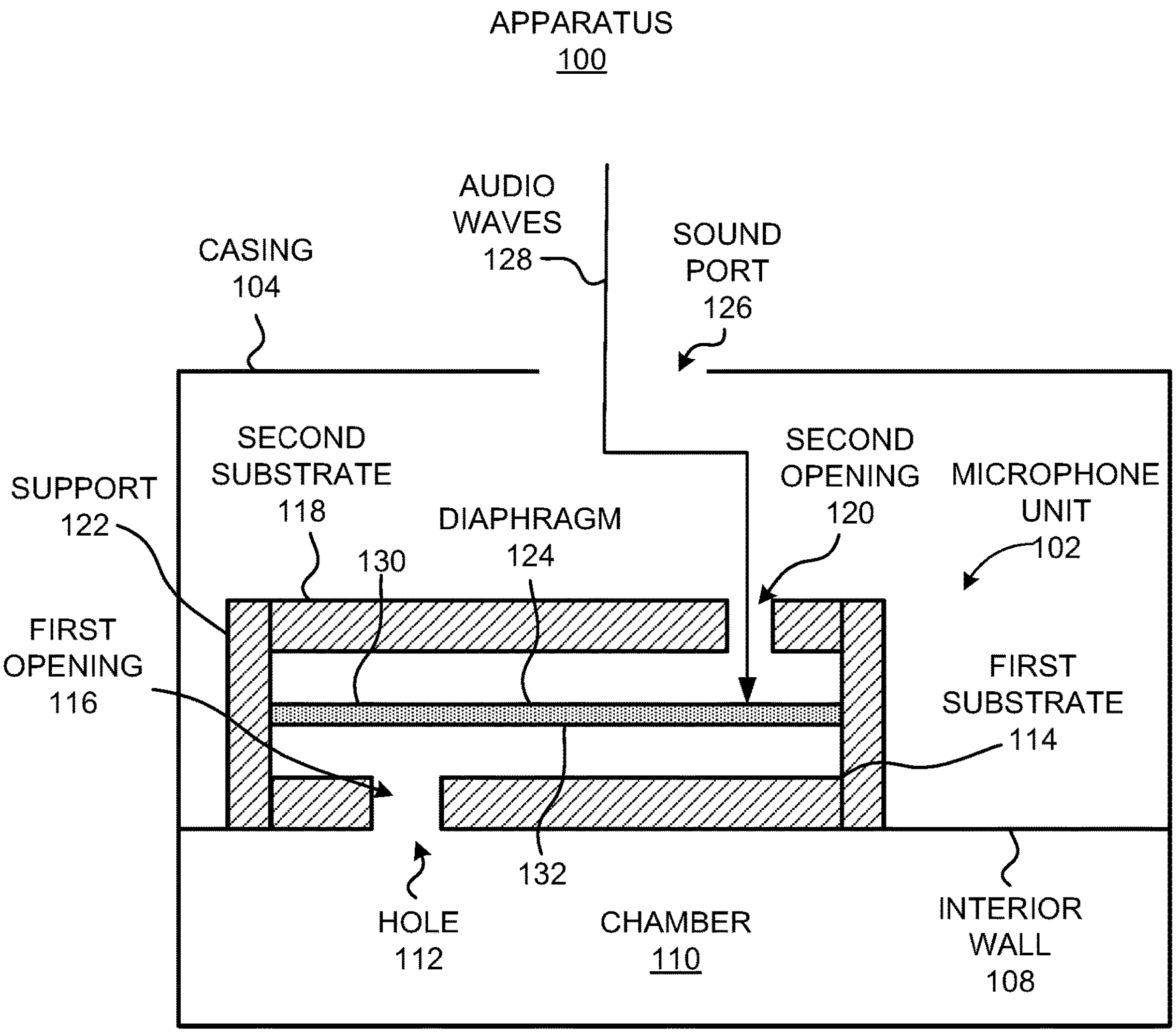
FIG. 1 shows a cross-sectional side view of an example apparatus including a microphone unit.

FIG. 1 shows a cross-sectional side view of an example apparatus 100 including a microphone unit 102. It should be understood that the apparatus 100 may include additional components and that some of the components described herein may be removed and/or modified without departing from a scope of the apparatus 100 disclosed herein.

According to examples, the apparatus 100 may be a microphone in a mobile telephone, a tablet computer, a headset, a portable studio microphone, or the like. The apparatus 100 may also be a microphone in an active noise control device. In any regard, the apparatus 100 may include a casing 104 (or housing), within which the microphone unit 102 may be housed. The casing 104 may be formed of plastic, metal, ceramics, or the like, and may include an interior wall 108 that is spaced from an exterior wall of the casing 104 such that a chamber 110 is formed within the casing 104. The interior wall 108 may also include a hole 112 that opens into the chamber 110 from an interior of the casing 104.

The microphone unit 102 may include a first substrate 114 that may be supported on or attached to the interior wall 108. In addition, the first substrate 114 may include a first opening 116 that is aligned with the hole 112 of the chamber 110 such that audio waves may flow through the first opening 116 and the hole 112. The microphone unit 102 may also include a second substrate 118 having a second opening 120. The second substrate 118 may be positioned with respect to the first substrate 114 to form a gap between the second substrate 118 and the first substrate 114. For instance, the microphone unit 102 may include supports 122 to which the first substrate 114 and the second substrate 118 may be attached. The microphone unit 102 may also include a diaphragm 124 attached to the supports 122. The first substrate 114 may also be recited herein as a first layer 114 and the second substrate 118 may also be recited herein as a second layer 118.

According to examples, the microphone unit 102 may be a microelectromechanical system (MEMS) device and the diaphragm 124 may be a MEMS diaphragm. In these and other examples, the diaphragm 124 may be a movable structure suspended from the supports 122. The microphone unit 102 may include circuitry or electronic components that may both sense movement of the diaphragm 124 and deliver the sensed movement data to a converter (not shown). The converter may convert vibrations of the diaphragm 124 into audio signals and/or electronic signals corresponding to the diaphragm 124 movements.

The casing 104 may include a sound port 126 through which audio waves 128, which are represented by an arrow, may be received into the apparatus 100. The audio waves 128 may cause the diaphragm 124 to vibrate as the audio waves 128 contact a front side 130 of the diaphragm 124. As shown in FIG. 1, the rear side 132 of the diaphragm 124 opposite the sound port 126 may be exposed to the chamber 110 through the first opening 116 and the hole 112. As a result, both the front side 130 and the rear side 132 of the diaphragm 124 may be exposed to areas that are larger than the gap in the microphone unit 102 between the first substrate 114 and the second substrate 118. By exposing the rear side 132 of the diaphragm 124 to the chamber 110, which may be a sealed volume other than through the hole 112, the microphone unit 102 may have an omnidirectional pickup pattern that may increase the available rear volume without increasing the size of the microphone unit 102 itself. In addition, the apparatus 100 may allow for lower frequency extension, flatter phase, lower noise, etc., than may be possible through use of the microphone unit 102 without making the microphone unit 102 larger.

Figure 2:
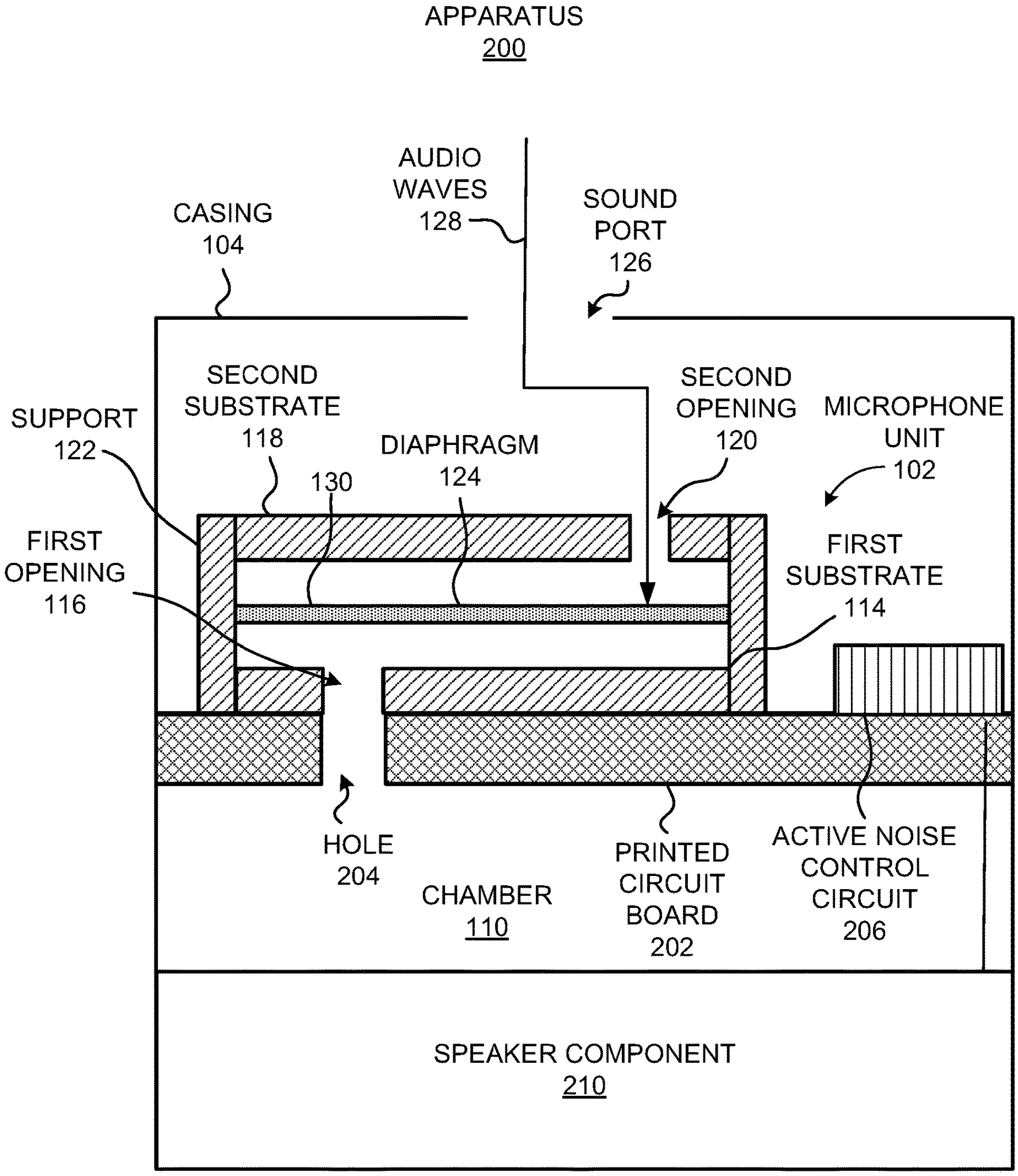
FIG. 2 shows a cross-sectional side view of another example apparatus including a microphone unit.

Turning now to FIG. 2, there is shown a cross-sectional side view of another example apparatus 200 including a microphone unit 102. It should be understood that the apparatus 200 may include additional components and that some of the components described herein may be removed and/or modified without departing from a scope of the apparatus 200 disclosed herein.

The apparatus 200 may include the same components as the apparatus 100 depicted in FIG. 1. However, the apparatus 200 may differ from the apparatus 100 in that a printed circuit board 202 may form the interior wall 108 of the casing 104 or may be attached to the interior wall 108 of the casing 104. In this regard, the printed circuit board 202 may divide the chamber 110 from the remainder of the casing 104 to form a volume that may be sealed from acoustic waves other than through a hole 204 in the printed circuit board 202. In addition, the hole 204 in the printed circuit board 202 may be aligned with the first opening 116 in the first substrate 114.

According to examples, electronic components, e.g., a circuit, an analog-to-digital converter, or the like, of the microphone unit 102 may be included in the first substrate 114. In addition, the electronic components may be connected to circuits in the printed circuit board 202 and the circuits in the printed circuit board 202 may control the output of electronic signals converted from the received audio waves 128. An active noise control circuit 206 that may perform active noise control using received acoustic signals from a conversion unit of the microphone unit 102 may be connected to the printed circuit board 202.

The apparatus 200, which may be a headset, a mobile device, a laptop computer, or the like, or a portion of a headset, a mobile device, a laptop computer, or the like, may further include a speaker component 210. The speaker component 210 may be mounted to the casing 104 (or equivalently, housing 104). The casing 104 may be shaped for insertion in a user's ear, while in other examples, the casing 104 may be shaped for placement over a user's ear. In still other examples, the casing 104 may be shaped for inclusion in a device, such as a mobile device, a laptop computer, a microphone, or the like. In any regard, the speaker component 210 may output audio signals, e.g., noise, music, etc., fora user to hear.

According to examples, the microphone unit 102, which may also be referenced as a microphone assembly, a device, or the like, and the active noise control circuit 206 may perform active noise control for the audio signals outputted by the speaker component 210. That is, the active noise control circuit 206 may be coupled to the microphone unit 102 to control ambient acoustic noise outside of the apparatus 200. For instance, the active noise control circuit 206 may produce an anti-noise signal designed to cancel background sound captured by the microphone unit 102 and the active noise control circuit 206 may drive the speaker component 210 with the anti-noise signal.

Figure 3:
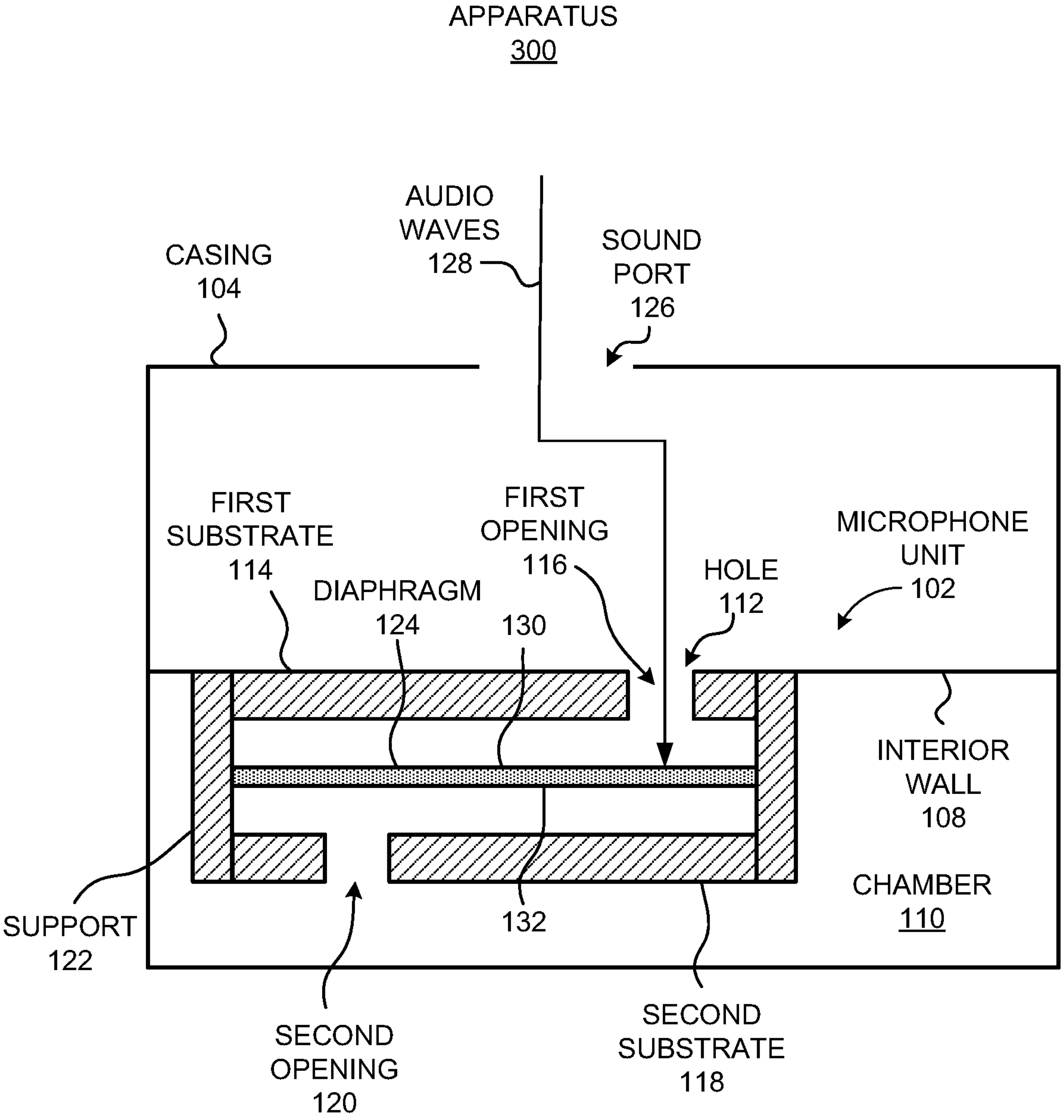
FIG. 3 shows a cross-sectional side view of a further example apparatus including a microphone unit.

Turning now to FIG. 3, there is shown a cross-sectional side view of another example apparatus 300 including a microphone unit 102. It should be understood that the apparatus 300 may include additional components and that some of the components described herein may be removed and/or modified without departing from a scope of the apparatus 300 disclosed herein.

The apparatus 300 may include the same components as the apparatus 100 depicted in FIG. 1. However, the apparatus 300 may differ from the apparatus 100 in that the microphone unit 102 may be housed within the chamber 110. That is, for instance, the first substrate 114 may be mounted or attached to the interior wall 108 of the casing 104, but on the side of the chamber 110. In this regard, audio waves 128 entering through the sound port 126 may enter through the hole 112 in the interior wall 108 and the first opening 116 to contact a front side 130 of the diaphragm 124. In addition, the rear side 132 of the diaphragm 124 may be exposed to the volume of the chamber 110 through the second opening 120. The chamber 110 may also be sealed other than through the hole 112 to create a closed volume in the chamber 110.

Figure 4:
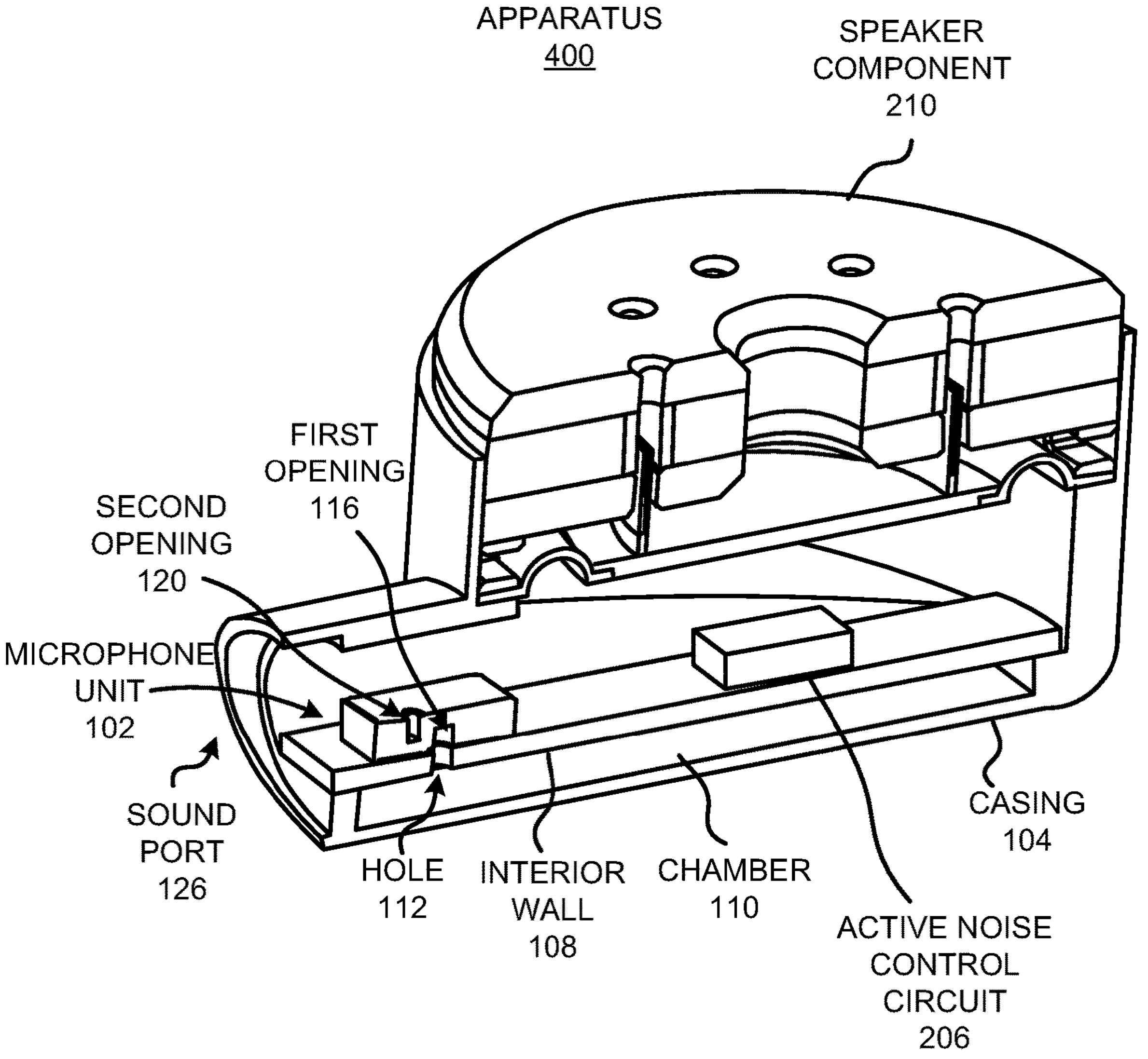
FIG. 4 shows a perspective view, in cross-section, of another example apparatus including a microphone unit.

With reference to FIG. 4, there is shown a perspective view, in cross-section, of another example apparatus 400 including a microphone unit 102. It should be understood that the apparatus 400 may include additional components and that some of the components described herein may be removed and/or modified without departing from a scope of the apparatus 400 disclosed herein.

As shown in FIG. 4, the apparatus 400 may include the same or similar features as those shown in the apparatuses 100-300 in FIGS. 1-3. However, the apparatus 400 is depicted as being suited for insertion into a user's ear canal. Particularly, the casing 104 may support a speaker component 210 that may be shaped for insertion into a user's ear canal. The casing 104 may also include a sound port 126 through which audio waves may flow into the apparatus 400 such that the microphone unit 102 may convert the audio waves into audio signals. The apparatus 400 may also include an active noise control circuit 206 that may be used with the speaker component 210 to perform active noise cancellation of sounds outputted by the speaker component 210 as discussed herein.

The casing 104 may also include the interior wall 108, which may be a printed circuit board 202 as shown in FIG. 2, that separates a volume of the casing 104 into a chamber 110. The interior wall 108 may also include a hole 112 that is aligned with a first opening 116 in the microphone unit 102. The microphone unit 102 may further include a diaphragm 124 and a second opening 120 as shown in FIGS. 1-3. Moreover, in other examples, the microphone unit 102 may be positioned inside the chamber 110 as shown in FIG. 3.

Although described specifically throughout the entirety of the instant disclosure, representative examples of the present disclosure have utility over a wide range of applications, and the above discussion is not intended and should not be construed to be limiting, but is offered as an illustrative discussion of aspects of the disclosure.

What has been described and illustrated herein is an example of the disclosure along with some of its variations. The terms, descriptions and figures used herein are set forth by way of illustration only and are not meant as limitations. Many variations are possible within the spirit and scope of the disclosure, which is intended to be defined by the following claims—and their equivalents—in which all terms are meant in their broadest reasonable sense unless otherwise indicated.

What is claimed is:

1. An apparatus comprising:
a chamber having a hole; and
a microphone unit including:
a first substrate having a first opening aligned with the hole of the chamber;
a second substrate attached to the first substrate to form an enclosure between the second substrate and the first substrate, the second substrate having a second opening; and
a diaphragm housed within the enclosure, wherein the first opening is positioned on a first side of the diaphragm and the second opening is positioned on a second side of the diaphragm.

2. The apparatus of claim 1, wherein the chamber is larger than the microphone unit and is sealed other than through the hole.

3. The apparatus of claim 1, wherein the diaphragm comprises a microelectromechanical system (MEMS) diaphragm.

4. The apparatus of claim 1, further comprising:
a housing, wherein the chamber is formed in the housing, wherein the housing comprises a sound port, and wherein the microphone unit is positioned adjacent to the sound port.

5. The apparatus of claim 1, further comprising:
a printed circuit board (PCB), wherein the PCB is to form a wall of the chamber, wherein the hole of the chamber is formed through the PCB, and wherein the microphone unit is mounted to the PCB.

6. The apparatus of claim 1, wherein the first substrate includes electronic components of the microphone unit.

7. The apparatus of claim 1, wherein the microphone unit is housed within the chamber.

8. A headset comprising:
a housing;
a speaker component mounted to the housing;
a volume formed in the housing, the volume having a wall with a hole;
a microphone assembly including:

a first substrate mounted to the wall, the first substrate having a first opening aligned with the hole of the wall;
a second substrate attached to the first substrate to form an enclosure between the first substrate and the second substrate, the second substrate including a second opening;
a diaphragm positioned in the enclosure; and
a conversion unit to convert movements of the diaphragm into acoustic signals.

9. The headset of claim 8, wherein the microphone assembly is housed within the volume.

10. The headset of claim 8, further comprising:
a printed circuit board (PCB) housed in the housing, wherein the PCB is to form the wall of the volume and wherein the hole of the volume is formed through the PCB.

11. The headset of claim 8, wherein the volume is sealed other than through the hole.

12. The headset of claim 8, wherein the housing comprises a sound port and wherein the microphone assembly is positioned adjacent to the sound port.

13. The headset of claim 8, further comprising:
an active noise control circuit to receive the acoustic signals from the conversion unit, the active noise control circuit to perform active noise control using the received acoustic signals.

14. An active noise control apparatus comprising:
a speaker;
an active noise control circuit;
a casing having an interior wall that is to block a section of the casing, the interior wall having a hole; and
a device including:
a first layer having a first opening, the first layer being mounted to the interior wall of the casing, wherein the first opening is aligned with the hole of the interior wall;
a second layer attached to the first layer to form an enclosure between the second layer and the first layer, the second layer including a second opening;
a diaphragm positioned in the enclosure, wherein the diaphragm is to vibrate as sound waves contact the diaphragm; and
a conversion unit to convert vibrations of the diaphragm into audio signals, wherein the active noise control circuit is to control the speaker to perform active noise control based on the audio signals.

15. The active noise control apparatus of claim 14, wherein the section of the casing is sealed other than through the hole.

* * * * *